(12) United States Patent
Palumbo

(10) Patent No.: US 7,528,951 B2
(45) Date of Patent: May 5, 2009

(54) OPTICAL DESIGN OF A MEASUREMENT SYSTEM HAVING MULTIPLE SENSOR OR MULTIPLE LIGHT SOURCE PATHS

(75) Inventor: Perry A. Palumbo, Fort Collins, CO (US)

(73) Assignee: Hach Company, Loveland, CO (US)

( * ) Notice: Subject to any disclaimer, the term of this patent is extended or adjusted under 35 U.S.C. 154(b) by 129 days.

(21) Appl. No.: 11/609,168

(22) Filed: Dec. 11, 2006

(65) Prior Publication Data

US 2007/0222984 A1 Sep. 27, 2007

Related U.S. Application Data

(60) Provisional application No. 60/785,074, filed on Mar. 23, 2006.

(51) Int. Cl.
*G01N 21/00* (2006.01)
(52) U.S. Cl. .......................... 356/338; 356/337
(58) Field of Classification Search .......... 356/335–343
See application file for complete search history.

(56) References Cited

U.S. PATENT DOCUMENTS

| | | | | |
|---|---|---|---|---|
| 3,612,689 | A * | 10/1971 | Liskowitz | 356/342 |
| 4,076,420 | A * | 2/1978 | De Maeyer et al. | 356/73 |
| 4,737,648 | A * | 4/1988 | Smith et al. | 250/559.21 |
| 4,854,705 | A * | 8/1989 | Bachalo | 356/336 |
| 4,931,767 | A * | 6/1990 | Albrecht et al. | 340/425.5 |
| 4,942,305 | A * | 7/1990 | Sommer | 250/574 |
| 5,506,679 | A | 4/1996 | Cooper | |
| 5,604,590 | A * | 2/1997 | Cooper et al. | 356/338 |
| 5,872,361 | A | 2/1999 | Paoli et al. | |
| 5,895,922 | A | 4/1999 | Ho | |
| 6,104,482 | A * | 8/2000 | Brower et al. | 356/239.4 |
| 6,413,786 | B1 * | 7/2002 | Hansen et al. | 436/526 |
| 6,519,033 | B1 * | 2/2003 | Quist et al. | 356/337 |
| 6,784,990 | B1 | 8/2004 | DeFreez et al. | |
| 7,057,724 | B1 * | 6/2006 | Mead et al. | 356/343 |
| 7,184,139 | B2 * | 2/2007 | Treves et al. | 356/237.2 |
| 2003/0116436 | A1 | 6/2003 | Amirkhanian | |
| 2003/0128363 | A1 | 7/2003 | Aberle | |
| 2004/0159799 | A1 | 8/2004 | Saccomanno | |
| 2005/0173638 | A1 * | 8/2005 | Powell | 250/341.1 |
| 2005/0225745 | A1 * | 10/2005 | Nagai | 356/73 |

FOREIGN PATENT DOCUMENTS

| EP | 0029662 A1 | 6/1981 |
|---|---|---|
| WO | WO-02/101339 A | 12/2002 |

* cited by examiner

*Primary Examiner*—L. G Lauchman
*Assistant Examiner*—Jarreas C Underwood
(74) *Attorney, Agent, or Firm*—The Ollila Law Group LLC

(57) ABSTRACT

A measurement system that has multiple sensors or multiple light sources is disclosed. The measurement system comprising a light source directed along a first axis and configured to illuminate a sample volume. The measurement system has a first sensor aligned along a second axis and is configured to detect scattered light in the sample volume. The measurement system has a second sensor aligned along a third axis and is also configured to detect scattered light in the sample volume.

14 Claims, 12 Drawing Sheets

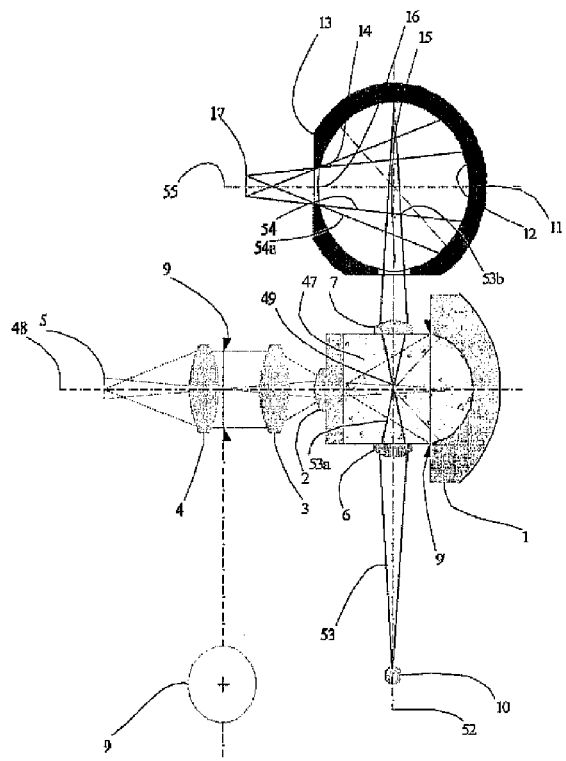
FIG. 7
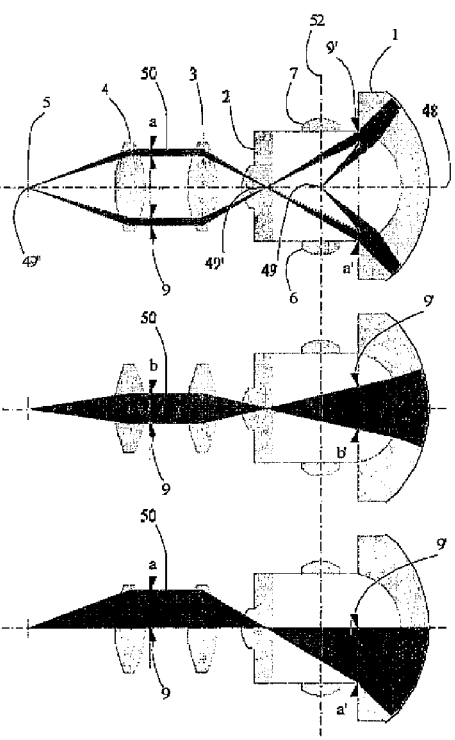
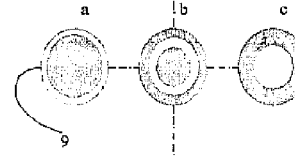
FIG. 7a
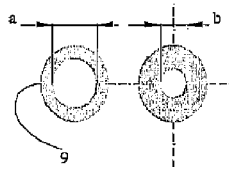
FIG. 7b
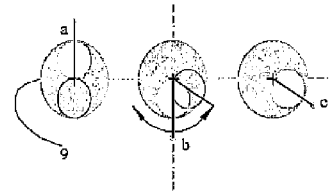
FIG. 7c

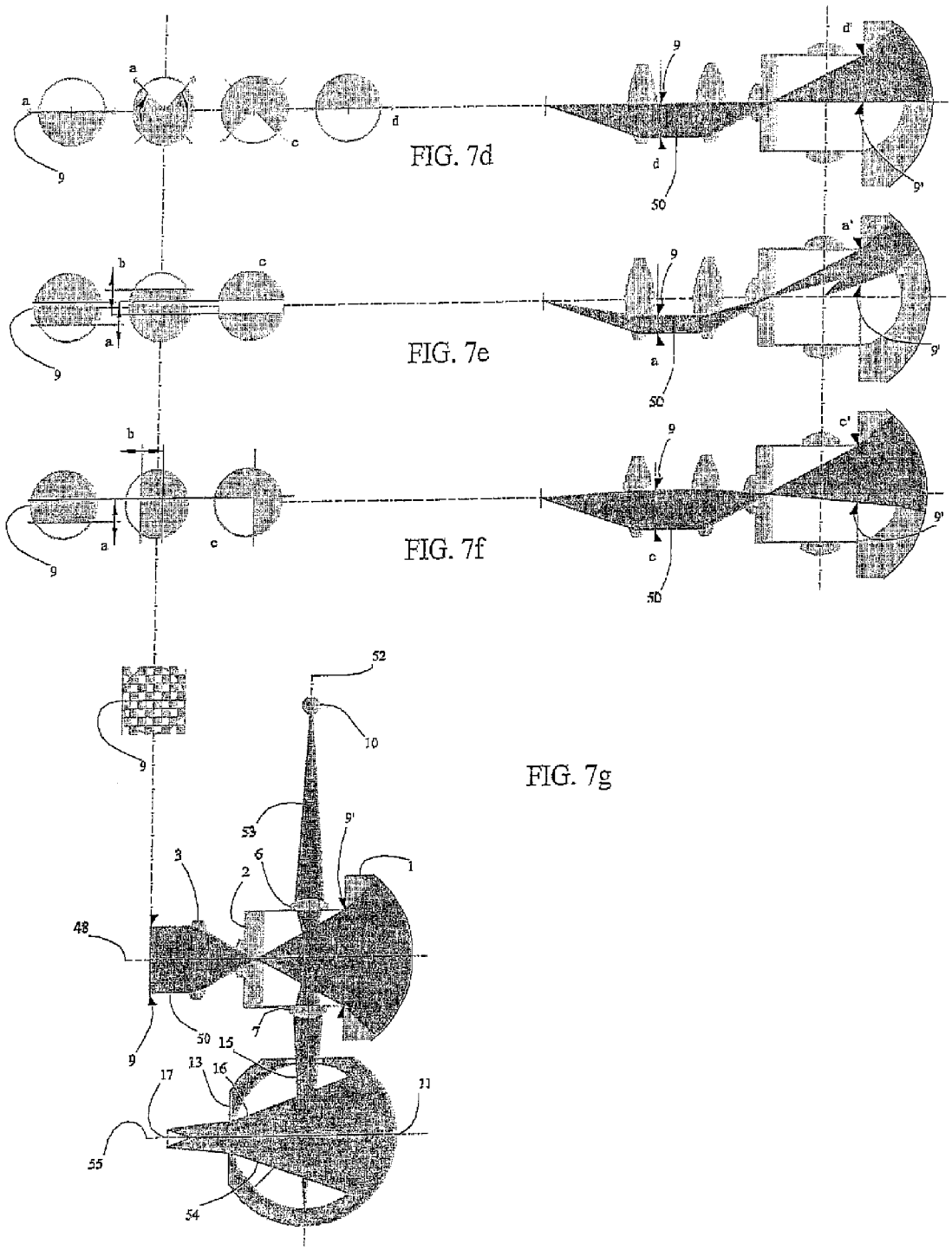

OPTICAL DESIGN OF A MEASUREMENT SYSTEM HAVING MULTIPLE SENSOR OR MULTIPLE LIGHT SOURCE PATHS

RELATED APPLICATIONS

This application claims the benefit of U.S. provisional application No. 60/785,074 filed on Mar. 23, 2006 entitled "Measurement of particulate matter in a media" which is hereby incorporated by reference into this application. This application is related to application "Measurement of light from a predefined scatter angle from particulate matter in a media", "Dual function measurement system", "Optical design of a particulate measurement system" and "Self calibrating measurement system" all filed on the same day as this application and are hereby incorporated by reference.

BACKGROUND OF THE INVENTION

Of interest to the process specialist, engineer, scientist, and others, is the quality or purity of product (media capable of particle suspension) being manufactured whether it liquid, gas, pharmaceutical, or the like. One measure of product quality is an assay of particulate matter or concentration of particulate matter within the end product or product during various stages of production so as to assure that particulate matter as a constituent of, or by product of the process, exists at a prescribed amount or within a suitable tolerance. When the particles in suspension are unknown, the particles may differ in composition, size, and shape. It is well known that matter interacts with light in a variety of ways, as example by means of absorption, reflection or scatter, and fluorescence to name a few. Various optical means have been devised to measure particulate matter within a suspension such as turbidimeter or nephelometer, particle counter, and densitometer but all use fundamentally different optical configurations each designed to measure a specific attribute or concentration range of the suspended particles by means of transmittance, reflection, or remittance of light.

Another constraint on the optical measurement configuration is imposed by regulatory agencies or by standardized methods by example the U.S. EPA Method 180.1, ASTM Standard Test Method for Turbidity of Water D 1889-00, and by International Standard ISO 7027 for the determination of turbidity for the assay of water quality. These methods and standards dictate the geometrical relationship of emitter to detector and the solid angle of collection optics so as to assure that instrument of similar task perform within designated parameters for reporting purposes.

Other limitations on devices for nephelometric measurement designed to determine the presence of particles in a suspension is the ability of the device to operate over a wide range of particle sizes and concentrations without impediment. Particle counters perform well at low concentration of particles but are prone to obstruction when the concentration or particle size becomes greater than the ability of the flow steam to pass through the narrow restriction, orifice, or capillary of the measurement interrupter. Devices, such as a turbidimeter, with unrestricted flow paths are insensitive to small concentrations of particles because the primary measurement technique relies on scattered light energy impinging on the detector means is greater than that of the self-generated noise of the detector.

Still another deficiency of devices used in the measure of particles in suspension is a lack of means to evaluate the operational readiness of the instrument without disruption of particle flow by the introduction of a calibration standard or calibration device, requiring interaction between a skilled operator or technician and the nephelometric device.

The disclosed invention eliminates the need for multiple nephelometric measuring devices and also system verification devices in order to perform assay of the presents or absence or number of suspended particles in a media as well as verification of the systems ability to measure in compliance to required performance attributes.

BRIEF DESCRIPTION OF THE DRAWINGS

FIG. 7—is a block diagram of the optical layout of the light source path in an example embodiment of the invention.

FIG. 7a to 7g—are block diagrams of various arrangements and constructions of an aperture masks used to discriminate angle of scatter from particles in suspension in an example embodiment of the invention.

DETAILED DESCRIPTION OF THE PREFERRED EMBODIMENT

FIGS. 1-12 and the following description and exhibit depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention.

As a result, the invention is not limited to the specific examples described below, but only by the claims and their equivalents.

Figure 1:
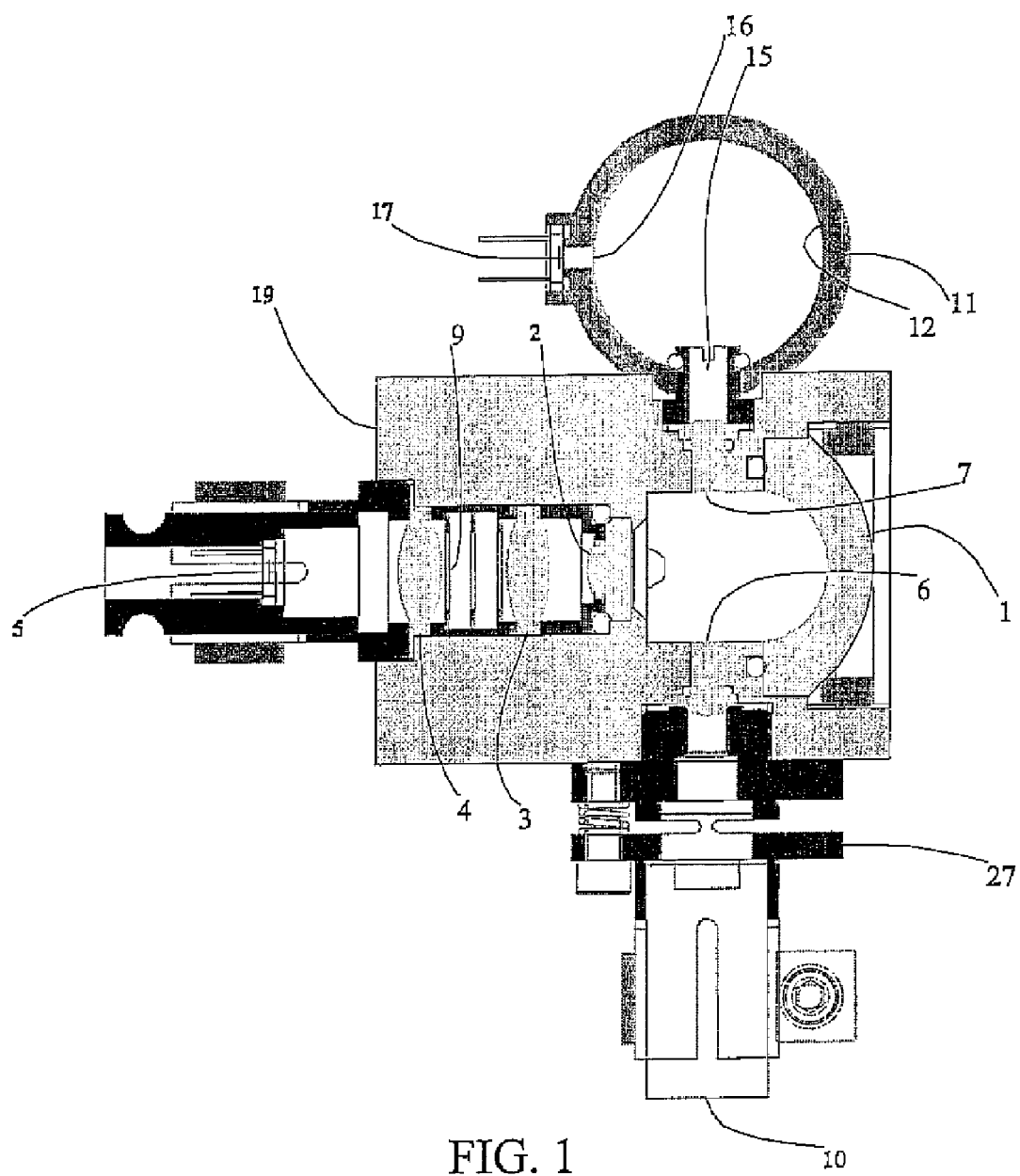
FIG. 1—is a sectional view of the optical layout of a particulate measurement system in an example embodiment of the invention.

FIG. 1 is a sectional view of the optical layout of a particulate measurement system in an example embodiment of the invention. Particulate measurement system comprises: light source 10, flexure mount 27, meniscus lens 1, input lens 6, output lens 7, field lens 2, device body 19, integrating sphere 11, transmit detector 17, lens 3, aperture mask 9, lens 4, and particle detector 5. Light source 10 is mounted in flexure mount 27 and projects a light along a first optical axis AA. Flexure mount 27 is used to adjust or align the angular relationship between light source 10 and device body 19. A cavity 8 is formed by meniscus lens 1, input lens 6, output lens 7, field lens 2, and device body 19. The media to be tested flows through cavity 8 along an axis perpendicular to the plane of the paper. Gaskets or sealing devices, for example O-rings, may be used between the lens and the device body to help form a fluid tight seal around cavity 8. Output lens 7 is mounted in device body 19 and aligned with first optical axis AA. Integration sphere 11 is mounted onto device body 19 near output lens 7. Integration sphere 11 has an entrance port 15 aligned with the first optical axis AA. Transmit detector 17 is mounted substantially 90 degrees to entrance port 15 at an exit port 16 of integrating sphere 11. Meniscus lens 1, field lens 2, lens 3, aperture mask 9, and lens 4 are aligned along a second optical axis BB. Particle detector 5 is mounted to device body and aligned with the second optical axis BB. The inside surface 12 of integrating sphere 11 may be preferentially coated to alter the reflectivity or enhance stability, durability, or maintainability of the reflective surface.

Figure 2:
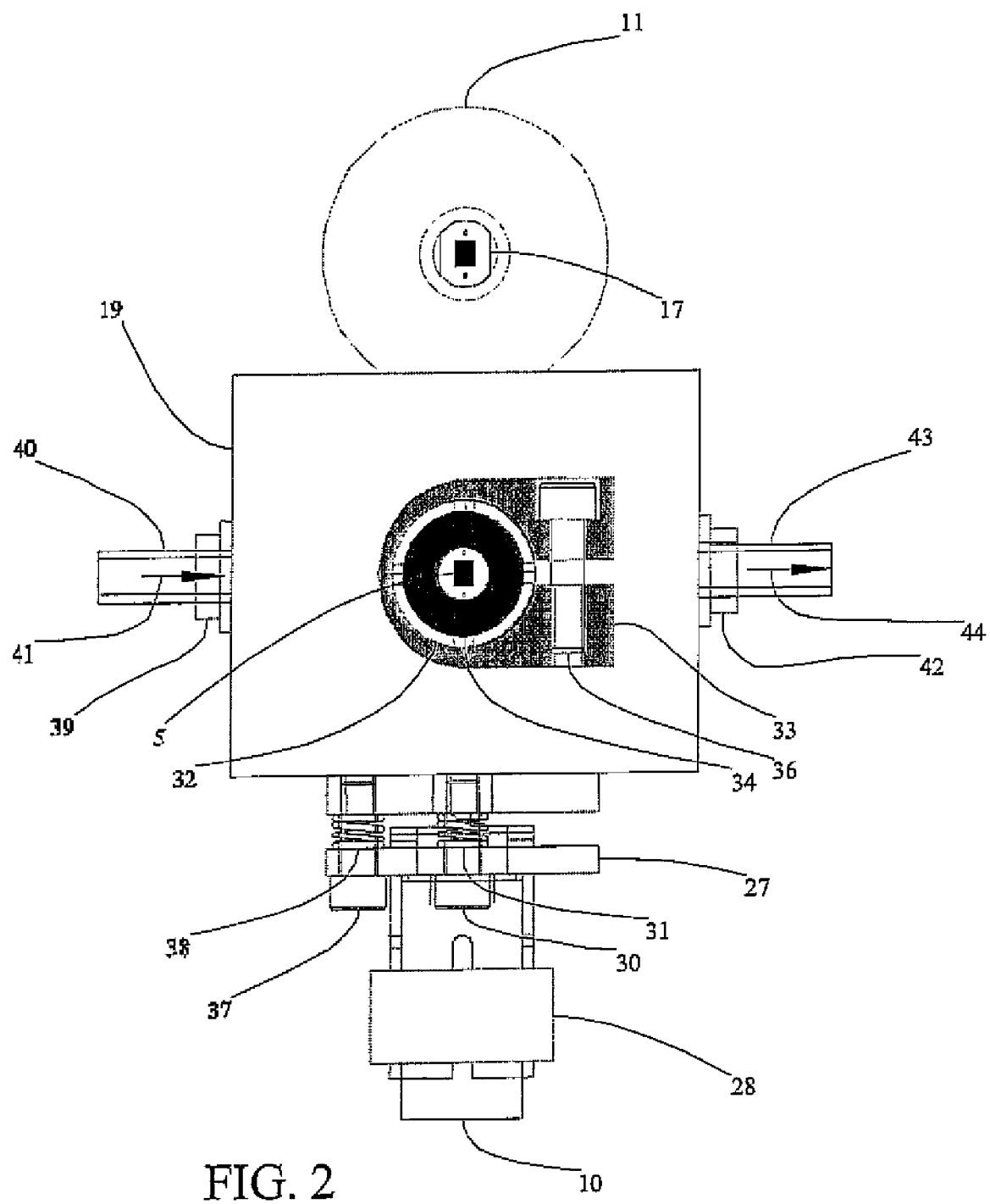
FIG. 2—is a first side view of particulate measurement system in an example embodiment of the invention.

FIG. 2 is a first side view of particulate measurement system in an example embodiment of the invention. Light source 10 may be that of a laser, LED, (Light Emitting Diode), incandescent lamp, or discharge lamp, or any other source of coherent or non-coherent radiation capable of stimulating the detector to produce useful information. The ingress 41 and egress 44 of a flow through the nephelometric device is carried by inlet tube 40 and outlet tube 43 facilitated by connection 39 and 42 attached to device body 19. A section view of clamp 33 in FIG. 2 shows the means by which screw 36 applies force to clamp 33 to squeeze detector sleeve 32 to secure detector holder 34 to a fixed position.

Figure 3:
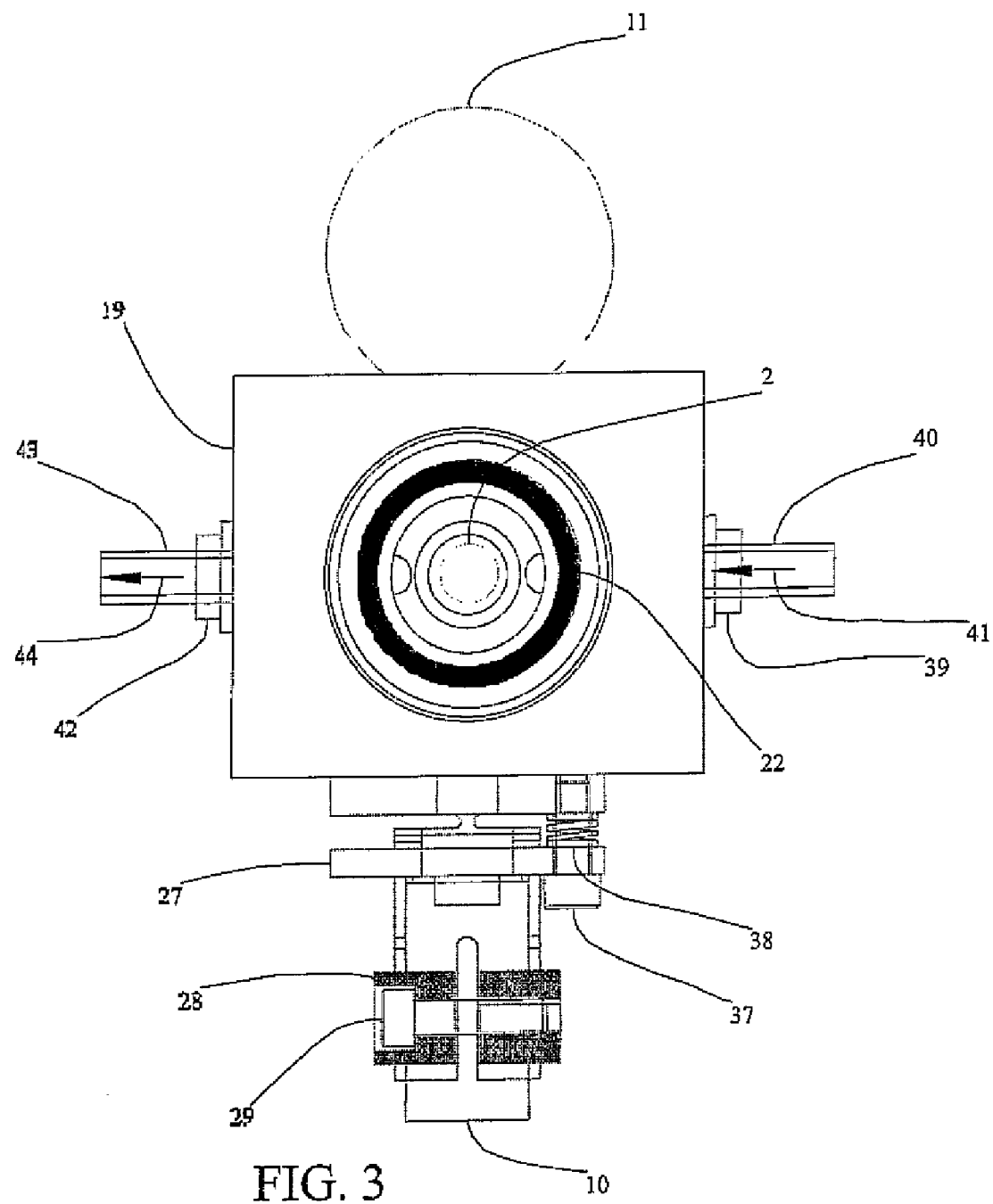
FIG. 3—is a second side view, with the meniscus lens removed, of a particulate measurement system in an example embodiment of the invention.

FIG. 3 is a second side view, with the meniscus lens removed, of a particulate measurement system in an example embodiment of the invention.

Figure 4:
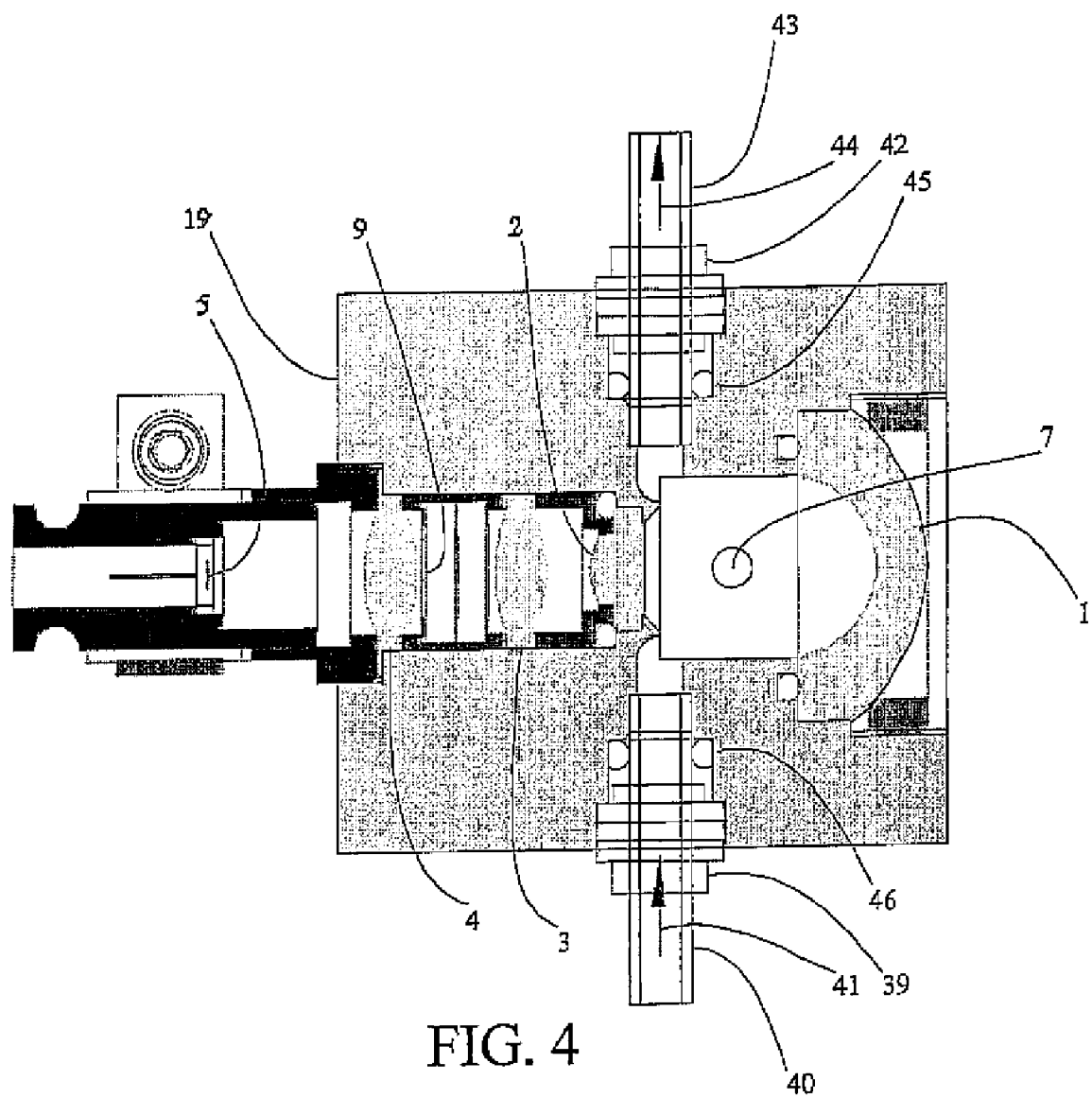
FIG. 4—is a sectional view of the flow path of a particulate measurement system in an example embodiment of the invention.

FIG. 4 is a sectional view of the flow path of a particulate measurement system in an example embodiment of the invention. Particulate measurement system comprises: meniscus lens 1, output lens 7, field lens 2, device body 19, lens 3, aperture mask 9, lens 4, particle detector 5, inlet tube 40 and outlet tube 43. The ingress 41 and egress 44 of a flow through the nephelometric device is carried by inlet tube 40 and outlet tube 43 facilitated by connection 39 and 42 attached, to device body 19. O-ring seals 45 and 46 seal tubing 43 and 40 to device body 19. The first optical axis AA forms a line perpendicular to the paper and is centered in output lens 7.

Figure 5:
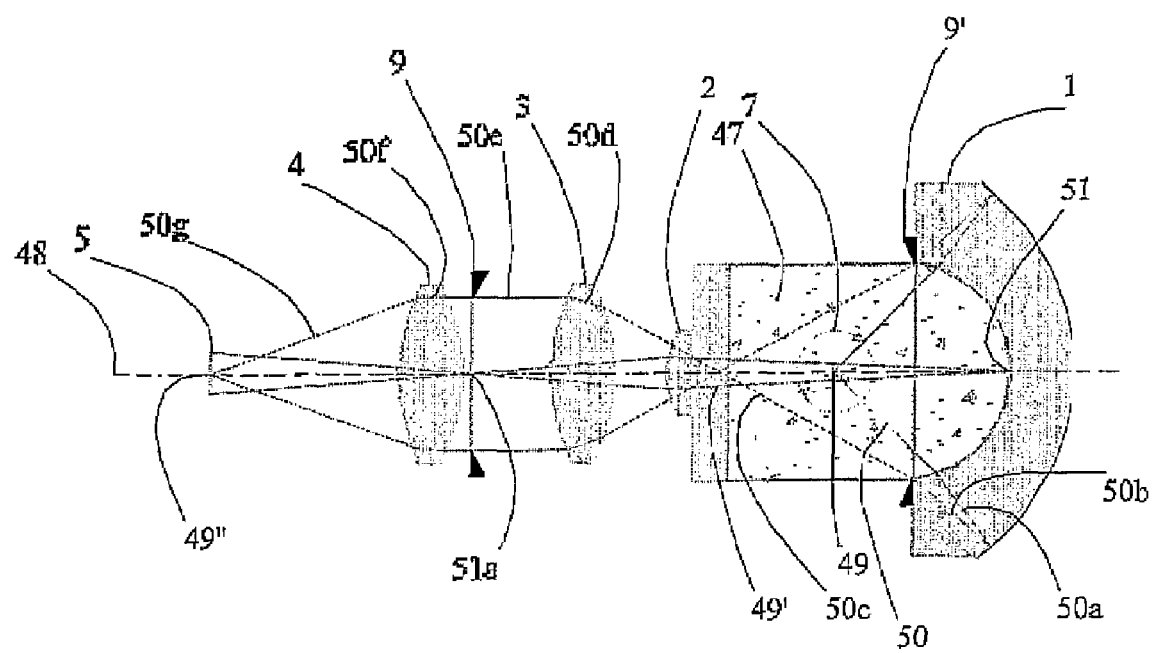
FIG. 5—is a block diagram of the optical layout of the detection path in an example embodiment of the invention.

FIG. 5 is a block diagram of the optical layout of the detection path in an example embodiment of the invention. FIG. 5 shows light scattered in the direction of meniscus lens 1 by particles in suspension media 47 at object plane 49. Meniscus lens 1, field lens 2, and lenses 3 and 4 along optical axis BB form an erect image at image plane 49" of the particle located at object plane 49. An intermediate image of the particles is formed by meniscus lens 1 along optical axis BB at image plane 49', within field lens 2. By forming the intermediate image within field lens 2 only that light which is reflected, scattered or emitted from particles toward meniscus lens 1 are brought to focus at image plane 49". As result, no image of particles in suspension is formed as direct result of lenses 3 and 4, but only as result of light impinging upon meniscus lens 1.

In one example embodiment of the invention, meniscus lens 1 is an emersion lens of refracting material greater than the refractive index of the suspension media. Meniscus lens 1 has a concave refracting first surface in contact with the suspension media, and a convex reflecting second surface. The first and second surfaces need not be concentric and neither surface needs be concentric with object plane 49. In one example embodiment of the invention the first refracting surface of meniscus lens 1 may be inert to the suspension media. Because the second reflecting surface of meniscus lens 1 is protected by the first refracting surface, meniscus lens 1 may be cleaned without danger of damaging the more delicate reflecting surface. The first refracting surface allows for an additional degree of freedom in the correction of optical aberrations that may otherwise degrade the image quality at image planes 49' and 49" without need of aspheric surfaces to the advantage of lower production cost. Because the main optical power of the meniscus lens is provided by the reflecting surface, problems with dispersion over a wide range of test wavelengths may be minimized. Marginal ray 50 from object plane 49 is refracted by the concave surface of meniscus lens 1, and propagates as ray 50a to reflective convex surface of meniscus lens 1. Upon reflection on the coated convex surface of the lens the reflected ray 50b is again refracted by the concave surface of the meniscus lens 1 and exits the lens as refracted ray 50c. Because object plane 49 and intermediate image plane 49', within field lens 2, are displaced along optical axis BB little refraction takes place on either side of field lens 2 as the index of refraction between suspension media 47 and index of refraction of field lens 2 are similar and the intermediate image 49' is concentric, or nearly so, to the convex surface of field lens 2. Meniscus lens 1 provides a large numerical aperture that captures a large portion of the light scattered from a particle in suspension media 47. In one example embodiment of the invention, in excess of ⅓ of the total scattered light may be utilized to impinge upon particle detector 5 at image plane 49". Marginal ray 50c is refracted by lens 3, as marginal ray 50d, and emerges from lens 3 as marginal ray 50e. Field stop 9 defines the extent to which marginal rays scattered from particle in suspension media 47 will propagate through the optical system. An image of field stop 9 is formed at or near the surface of meniscus lens 1 as field stop image 9'. Marginal ray 50e propagates to lens 4 and is refracted as marginal ray 50f, emerging from lens 4 as marginal ray 50g where an erect image of the particle is formed from the scatted light from object plane 49 at image plane 49". Principle ray 51 follows a similar path through the optical system passing through the center of field stop 9 and also through the center of the image 9' of the field stop formed at the surface of meniscus lens 1. Field stop 9 is positioned from lens 4 such that particle detector 5 is at the infinite conjugate of field stop 9. Thus, any portion of the image formed at field stop 9 impinges equally at the surface of particle detector 5.

Detector 5 may be that of a photodiode, Photo-Multiplier Tube (PMT), Charged Coupled Device (CCD) or Complementary Metal Oxide Semiconductor (CMOS) image sensor, or any other means to convert light or radiation into quantifiable values of electrical potential or current. In one example embodiment of the invention, area array detectors such as CCD or CMOS image sensors may be used to measure by spatial position and incremental area the intensity of the image formed on the image sensor. Using this information, the device may measure size, shape, distribution, occurrence, and velocity of the particles in suspension at object plane 49. The magnification of object to image along optical axis BB is selected to provide adequate resolution for the measurements of interest and defines the maximum area that can be measured in the suspension. If the size of the image sensor is 6.4×4.8 mm and the magnification of the optical system is 2×, then the maximum area that can be measured in the suspension is 3.2×2.4 mm. For a given image sensor a fixed number of photosensitive sites are present as example 640×480 pixels, therefore each pixel is 10 um and represents a resolution of 5 um object per pixel in suspension. If the particles to be measured are at least 2 to 3 times larger than the resolution of the system, then a reasonable measure of the size and shape of the object can be determined. The depth of the image along optical axis BB is a result of the diameter or width of the illuminating beam along optical axis BB and, or the depth of field of the imaging optical system. A defined measurement volume may be determined using the width of the illumination along optical axis BB, the depth of field of the imaging optical system, the magnification of the optical system, and the size of the particle detector. A count of the illuminated particles or fluorescent particles within the defined measurement volume may be reported as a count per cubic millimeter. If the image sensor is of an integrating type, as the case for CCD and CMOS image sensors, the integration time—the time allotted for charge to accumulate on the photosensitive area of the device, may be used to determine the flow rate of the particles in suspension by measure of the number of pixels transgressed during the integration period. The resulting image is sometimes referred to as a "streak", the length of which and the known integration time can be used to calculate the velocity of the particle, hence the flow rate of the suspension media. When the concentration of particles in suspension is sufficiently high, individual particles become indistinguishable at the image sensor but may be measured as a concentration of particles by means of the total charge accumulated during the known integration period on the image sensor, or ampere current product of particle detector 5 as that of a photodiode, that is correlated to Nephelometric Turbidity Units (NTU), Formazin Nephelometric Unit (FNU), McFarlane Units, or other standard nephelometric unit of measure of the cloudiness or haze of the suspension calibrated to a known concentration of nephelometric standard.

Figure 6:
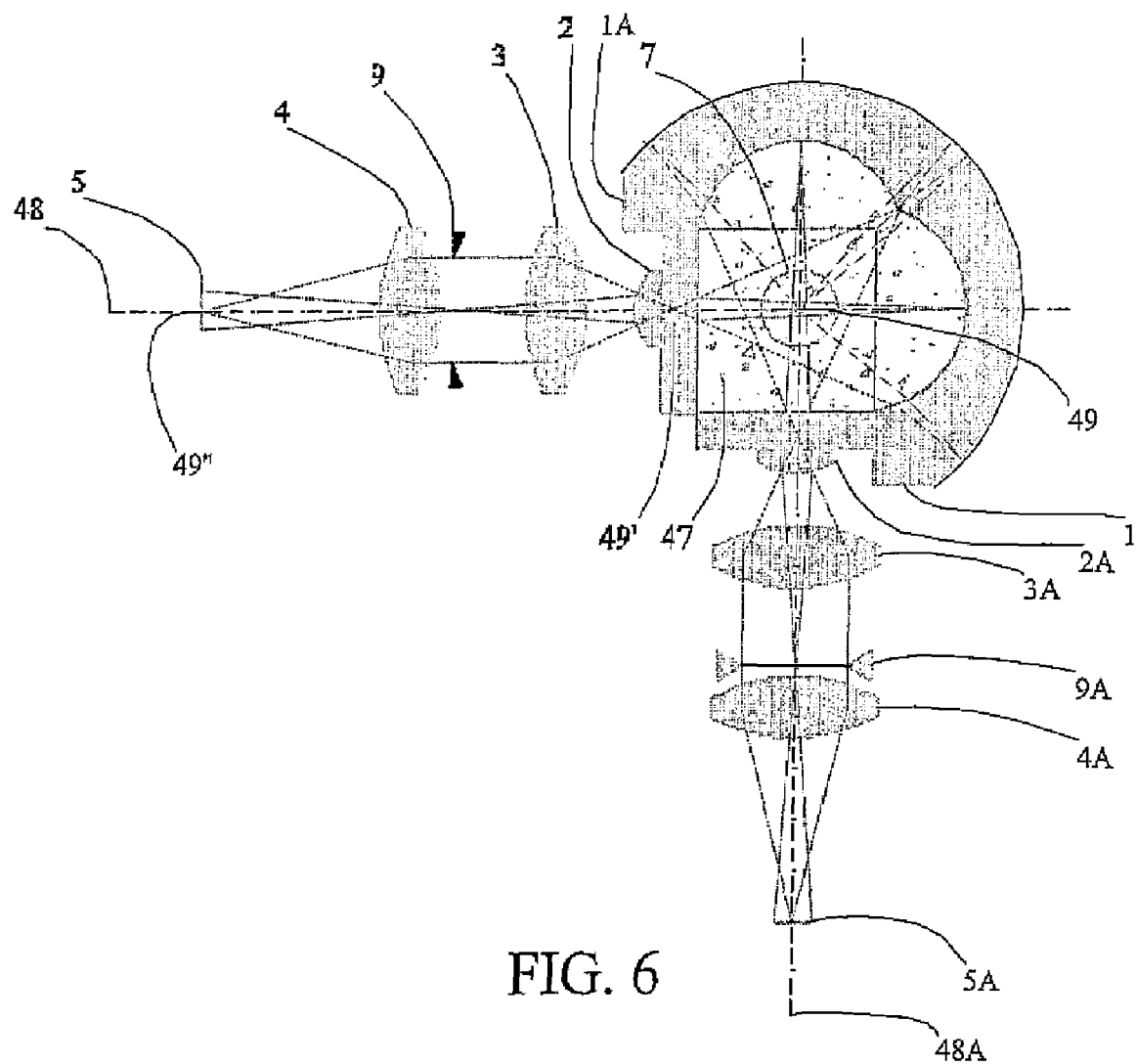
FIG. 6—is a block diagram of the optical layout when utilizing more than one detection path in an example embodiment of the invention.

The disclosed invention is not limited to a single detection path. FIG. 6 is a block diagram of an optical layout when utilizing more than one detection path in an example embodiment of the invention. A second optical axis CC is introduced at substantially 90 degrees to optical axis BB, both at substantially 90 to the optical axis of the light source. Light scatter from particle at object plane 49 is collected and transmitted along optical axis CC in the same manor as described for that of FIG. 5 utilizing instead meniscus lens 1A, field lens 2A, lenses 3A and 4A, to form an erect image of the particle at particle detector 5A. The two images are related, as the image formed at particle detector 5A is the image profile of the image formed at particle detector 5. In addition the two detectors, 5 and 5A need not have the same spectral response nor is there a need for meniscus lens 1 and 1A to have the same spectral reflectivity. Indeed each optical path may be altered by the addition of optical filters or by means of coating reflectivity or by detector response such that each optical path is sensitive to different portion of the spectra so as to detect absorption or emission from particles in suspension media 47 at object plane 49 at unique wavelength(s).

FIG. 7 is a block diagram of the optical layout of the light source path in an example embodiment of the invention. It is desired to keep stray radiant energy from propagating along optical axis BB to particle detector 5. It is therefore best practice not to illuminate more of the sample volume than that which can be imaged on to particle detector 5. Input lens 6 focuses light 53 as 53a from light source 10 to illuminate that sample volume to which will contribute an image of the sample volume at particle detector 5. After light has propagated through the sample volume, output lens 7 directs the transmitted light, not absorbed or scattered by the particles in suspension as light 53b, into the entrance port 15 of integrating sphere 11. Coatings or finish on the inside surface 12 of the integrating sphere 11 are optimized to be diffusely reflective so as to uniformly illuminate the inside surfaces of the integrating sphere with the transmitted light. In so doing transmit detector 17 will measure the same intensity of light regardless of the exact angle or distribution of light within the transmit beam of light source 10 along optical axis of illumination AA. Exit port 16 in the integrating sphere 11 is positioned at substantially 90 degrees to the entrance port of integrating sphere 11. So as to prevent direct illumination of transmit detector 17 and thus reduce the sensitivities to beam incidence and position, the lines of sight of the detector 54 and 54a of the transmit detector 17 does not include entrance port 15 or the incident transmit energy on the inside surface 12 of integrating sphere 11. Signals generated from transmit detector 17 and particle detector 5 can be utilized to determine the ratio of transmitted light to scatted light or to measure the absorption or fluorescence of particles. Another advantage of the novel use of an integrating sphere for the measure of transmitted light in a nephelometer is due to the redistribution of light across the inner surface 12 of integrating sphere 11, resulting in a decrease in surface intensity at the transmit detector 17, thereby eliminating the need for light traps or neutral density filters to reduce the maximum value for incident light impinging on the transmit detector 17.

A unique quality of the disclosed invention is the ability to image an object or mask, positioned along optical axis BB at field stop 9, onto or near the surface of meniscus lens 1. As shown in FIG. 7a, an annular mask 9a place at the location of field stop 9, is utilized to discriminate by permissible propagation only those rays which are reflected or scattered from object plane 49 at a high angle relative to optical axis BB. Annular masks 9b and 9c used in lieu of stop 9 are utilized to change the permissible propagation angle of scatter while maintaining a constant optical system etendue. Etendue is used to specify the geometric capability of an optical system to transmit radiation, its throughput. The numeric value of the etendue is typically a constant of the system and gets calculated as the product of the opening size and the solid angle that the system accepts light from. Etendue may also be known as the collecting or light gathering capability of an optical system. An iris diaphragm, as shown in FIG. 7b, substituted for fixed field stop 9 of FIG. 7 can be adjusted to alter the amount of light impinging on particle detector 5 and also the total included angle of scatter from object plane 49. Light scattered from a particle(s) towards the incident beam of illumination is referred to as "back scatter" in nephelometric terms. Conversely, light scattered away from the source of illumination is referred to as "forward scatter". Light scattered from a particle neither toward or away from the incident light source is referred to as "side scatter" in nephelometric terms. Apertures or masks in the forms as shown in FIG. 7c through FIG. 7g permit measurement of the amount, by scatter type, of light scatted from a particle(s). This is useful so as to be able to measure different concentrations of particles, as different types of scatter are more useful as to linearity or sensitivity depending on the concentration of particle(s) in the suspension media. A circular mask offset from optical axis BB placed at the position of field stop 9 of FIG. 7, as in FIG. 7c, is rotated eccentric to optical axis BB as 9a, 9b, and 9c, to keep constant the etendue of the optical system with preferential selection of the scatter angle about optical axis BB as a conic section. Two semi-circular masks rotated independently about optical axis BB laminated in close proximity to one another at the position of field stop 9 of FIG. 7 is shown as 9a, 9b, 9c, and 9d in FIG. 7d. Rotation of the masks independently creates a sector aperture through which a portion of scattered light about optical axis BB is permitted to pass through the optical system to particle detector 5 at the selected direction of scatter. A mask in the form of a shutter(s) is utilized to select an angular portion of the scatted or emitted light from object plane 49 as shown in FIG. 7e. A shutter is slide across the face of aperture 9 of FIG. 7 to preferentially transmit or block the propagation of rays to particle detector 5 dependent on the angle of scatter of emission from object plane 49. The shutter in position 9a of FIG. 7e transmits light that is forward scattered from object plane 49. Two shutters independently adjustable orthogonal to each other laminated in close proximity at the position of field stop 9 of FIG. 7 is shown in FIG. 7f. The aperture, a sector, formed by the two shutters can be translated off optical axis BB unlike that of the sector formed by the semi-circular masks of FIG. 7d. A pixilated mask at position of field stop 9 controlled by means of selective polarization of the scattered light passing through a polarizing film and electrically polarized liquid crystals as in a transmission LCD, (Liquid Crystal Display), is utilized to block, by means of cross polarization, light from propagating through said LCD along optical axis BB. A pixilated mask can be substituted for any or all of the described forms of apertures previously described without preference. The choice of the mask effectively selects the angles of reflection that detector 5 will eventually process. Alternately, when only the angle and or intensity of scattered or emitted light is to measured from object plane 49 and no image need be formed of the scattering particle(s), as in the case of presence of particles or fluorescence, then a image array such as a CCD or CMOS image plane sensor is placed in substitution to field stop 9 as shown in FIG. 7g. Light impinging on pixels of the image plane sensor is thus discriminated by angle of scatter or emission since an image of the pixel is formed at the surface of meniscus lens 1 as field stop image 9'. Using the optical layout having multiple detection paths as shown in FIG. 6, multiple masks may be used having different masking areas, such that different measurements of the angle of scatter for particles may be made simultaneously.

Figure 8:
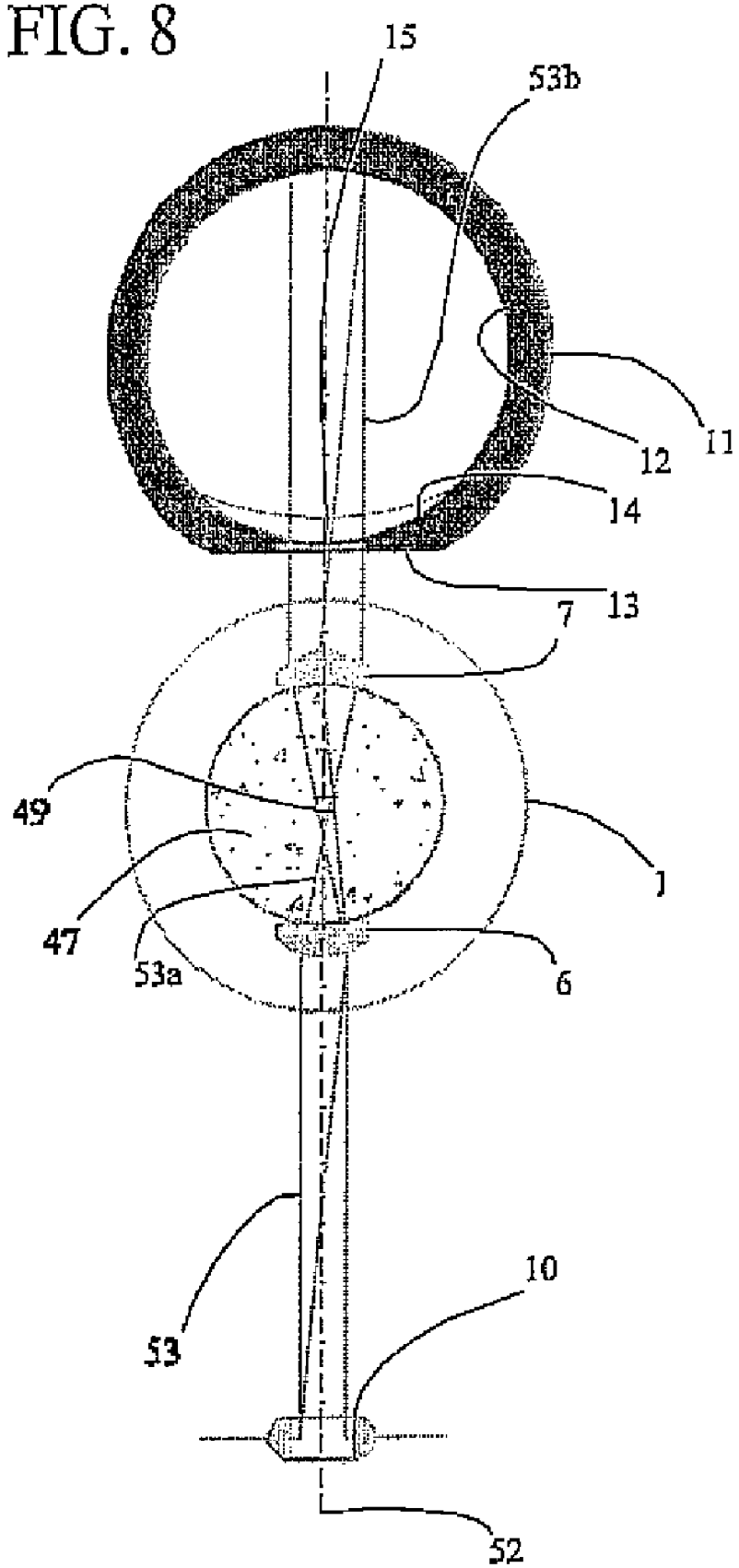
FIG. 8—is a block diagram of the optical layout of the view area of the suspension media in an example embodiment of the invention.

FIG. 8 is a block diagram of the optical layout of the view area of the suspension media in an example embodiment of the invention. Light from light source 10 propagates as marginal ray 53 to input lens 6 to form a caustic of illumination or focused image of the source at the object plane 49. Light not scattered or absorbed continues along optical path AA to exit lens 7 where upon the unabsorbed or light not scattered by particulate matter is relayed to inside surface 12 of integrating sphere 11 through input port 15. Alternately lenses 6 and 7 need not have optical power in the case where the light being emitted into the suspension media is collimated or focused and the subtended angle into integrating sphere is small. Lenses 6 and 7 may be completely removed in the case where the suspension media need not be isolated from the external elements of the device, for example when the particles are suspended in air or some other gas or vapor.

Figure 9:
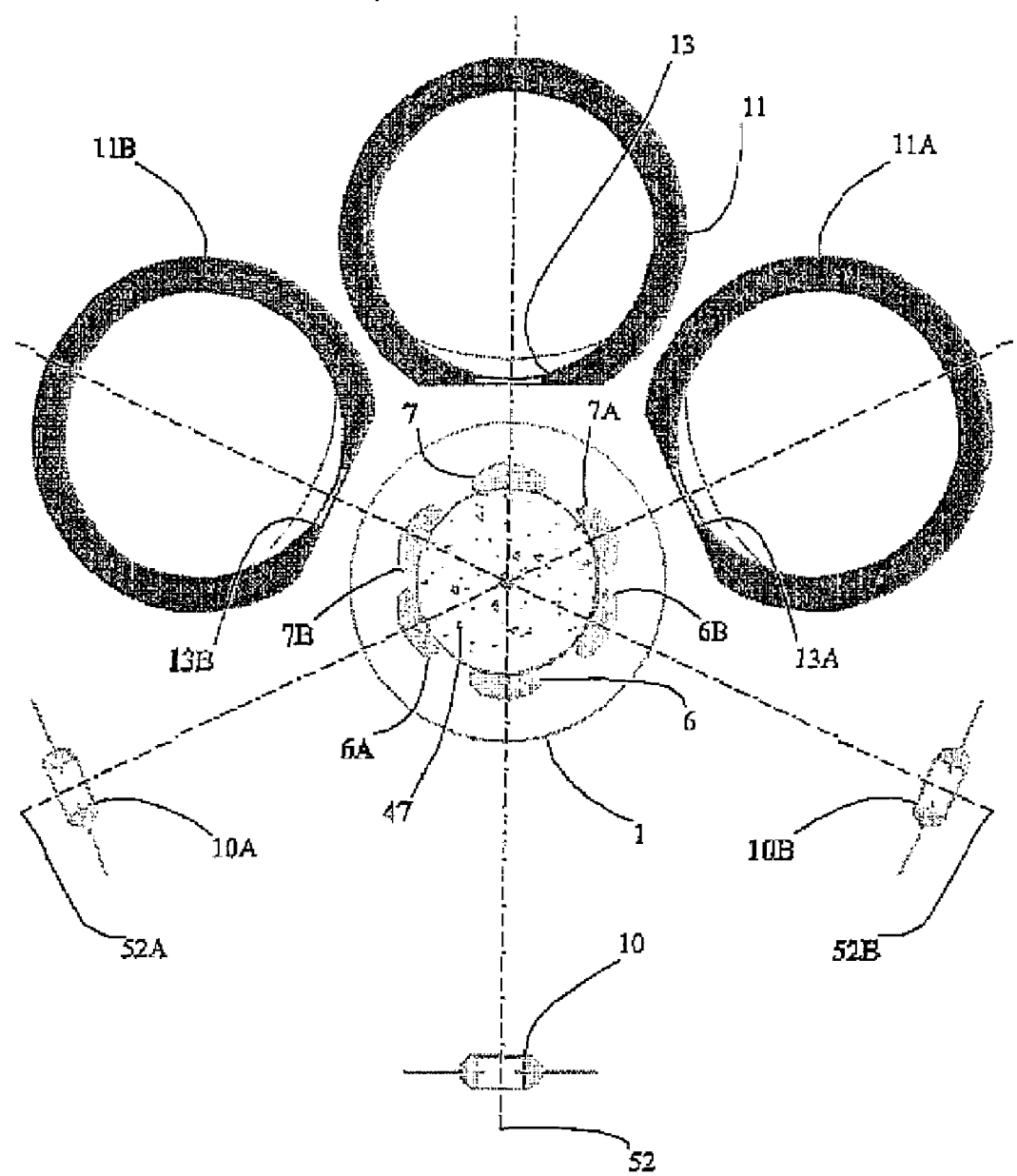
FIG. 9—is a block diagram of a particulate measurement system utilizing a plurality of light source paths in an example embodiment of the invention.

In one example embodiment of the invention, a plurality of illumination paths may be used. FIG. 9 is a block diagram of a particulate measurement system utilizing a plurality of light source paths in an example embodiment of the invention. FIG. 9 has light sources 10, 10a and 10B projecting illumination along optical axis 52, 52A, and 52B. In one example embodiment of the invention light source 10, 10A and 10B need not have the same spectral emission or may have selected wavelength(s) of emission of by the introduction of optical filter material along optical axis 52, 52A, or 52B, or by judicial selection of optical materials or coatings used for lenses 6, 6A, 6B and, or lenses 7, 7A, and 7B.

Figure 10:
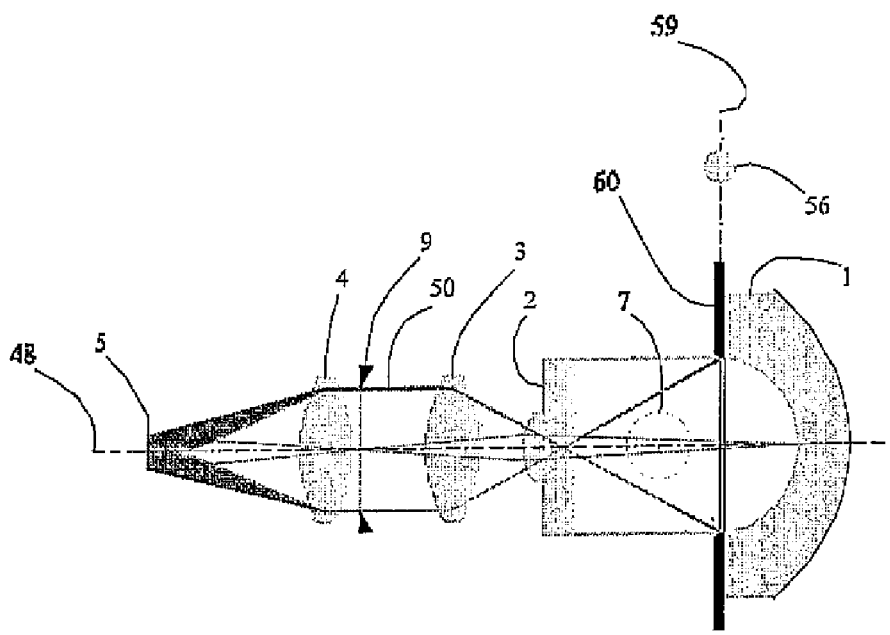
FIG. 10—is a block diagram of the optical layout of a particulate measurement system with an annulus virtual source and second light source in an example embodiment of the invention.

Another aspect of the present invention is the ability to introduce light into the detection path(s) of a known amount or percentage so as to facilitate the calibration or verification the operational readiness of the device without disruption to the flow or particle stream. A non-disruptive calibration or verification is accomplished by the introduction of light within the field of view of the detection optics along optical axis BB at the image plane of the field stop 9', synonymous to the surface of meniscus lens 1, as shown in FIG. 10. Annular waveguide 60, of transparent plastic glass, or other suitable materials, transports light from second light source 56 along optical axis 59 between the two face surfaces by means of Total Internal Reflection, (TIR), from outer edge of annular waveguide 60 to inner edge of annular waveguide 60. The inner edge of annular waveguide 60 may be preferentially ground, etched, or coated so as to scatter light along optical axis BB as an annulus of marginal rays to form an image of annular waveguide 60 at field stop 9 and subsequently impinges equally onto particle detector 5 since particle detector is at the infinite conjugate of lens 4. By selectively permitting second light source 56 to emit light at a known intensity, by provision of electrical or mechanical means, light is introduced along optical axis BB in addition to light scattered or emitted from particles stimulated by light source 10. Since light introduced by light source 10 must travel through the suspension media the light is affected by the concentration of particles in the suspension media by means of absorption, scatter, and emission of light in the same manor as the transmitted light from light source 10 to transmit detector 17. The ratio of the amount of transmitted light to detector 17 from light source 10 to the amount of light transmitted from second light source 56 to particle detector 5 is constant provided light source 10 and second light source 56 emit at a constant intensity and that all optical surfaces degrade in like manor. An abnormal condition exists as result of the ratio from the established value is in deviation by more than a prescribed amount as to warrant action for either correction of the abnormal condition or to compensate of the ratio so as to restore the ratio to the established value.

Since lenses 3 and 4 relay an image from within field lens 2 it is also possible to utilize this arrangement to opt for a material or construction for field lens 2 that will partially scatter by applied electrical field or other stimulation cause field lens 2 to change optical characteristics to the objective as to redirect light emitted into the edge of field lens 2 by means of scatter or to emit light within field lens 2 along optical axis BB and thus impinge upon particle detector 5. This arrangement has the advantage of the light scattered or emitted is unimpeded and not transmitted through the suspension media and is unaffected by biological films or depositions of materials that come in contact with the suspension media, thus a more stable and reproducible calibration or verification source is result.

Figure 11:
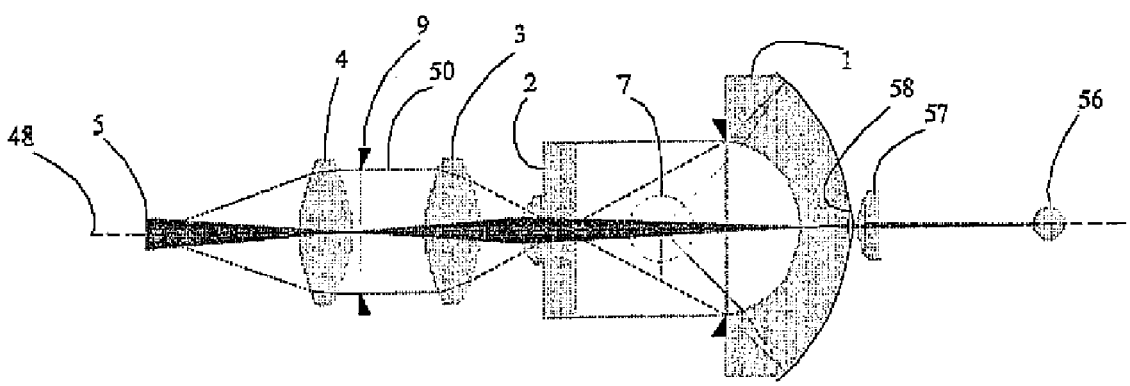
FIG. 11—is a block diagram of the optical layout of a particulate measurement system with an uncoated area of the convex lens surface and a second light source in an example embodiment of the invention.

Alternately light may be introduced along optical axis BB through a central uncoated portion or aperture 58 in the optical coating of the convex surface of meniscus lens 1 as shown in FIG. 11. An image of second light source 56 is brought to focus at the concave surface of meniscus lens 1 synonymous with image 9' of field stop 9, by lens 57 through the uncoated central aperture 58 in meniscus lens 1. The alternate scheme for the introduction of light from a second light source differs from the previously described method of FIG. 10 since no physical radiator is present at concave surface of meniscus lens 1 but instead an image of second light source 56, and that the light comprised of principle rays and not marginal rays. The light impinging on particle detector 5 is however indistinguishable in result between the method of light introduction of FIG. 10 and FIG. 11 as both effectively emit light at image plane 9' of field stop 9 within the field of view of the detection optics along optical axis B.

Figure 12:
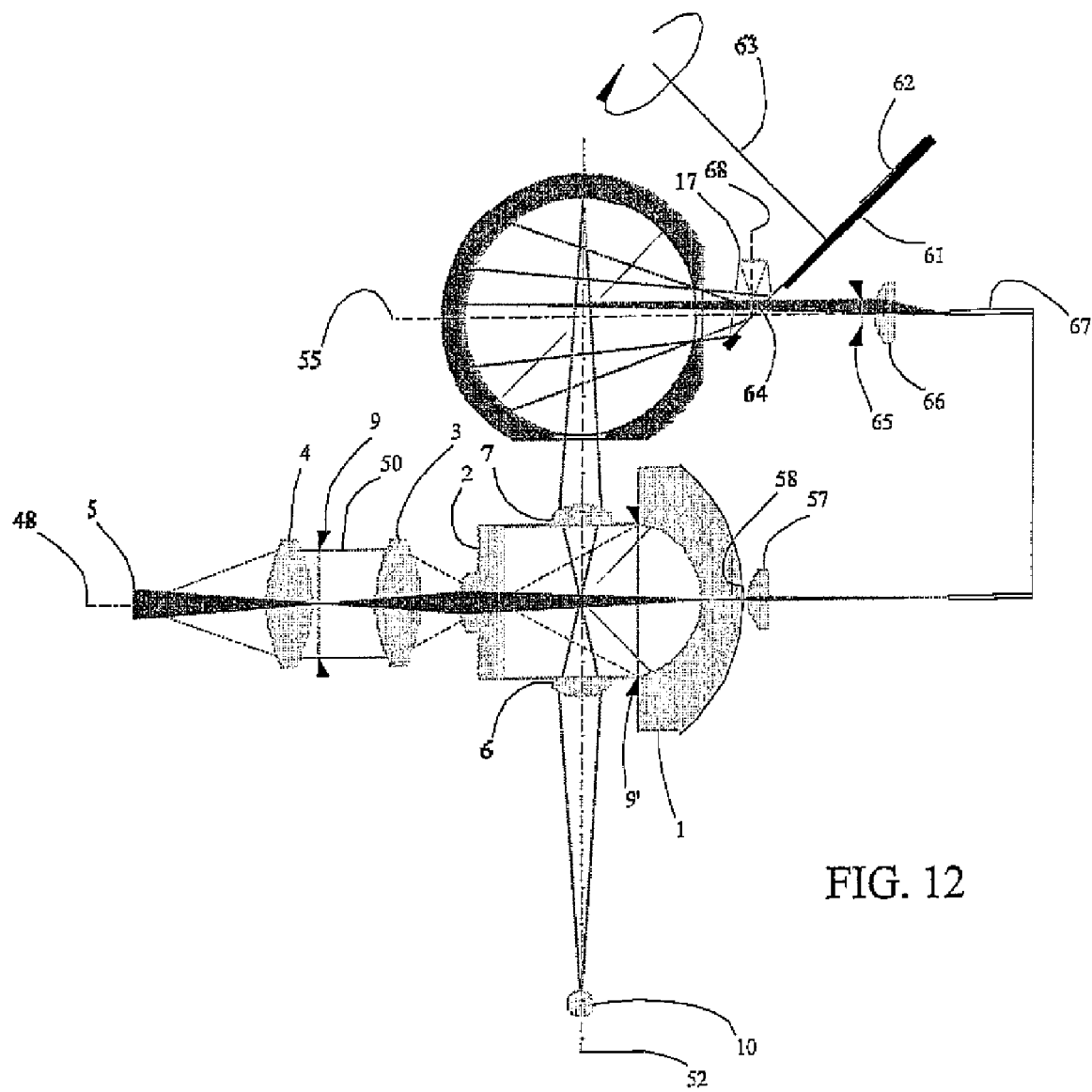
FIG. 12—is a block diagram of the optical detail of an insitu calibration and verification means utilizing light from the primary light source and optical switching means to divert a portion of the primary source to the calibration and verification means in an example embodiment of the invention.

Another means to introduce light along the optical axis BB for the purpose of calibration or verification of operational readiness is disclosed for the present invention without the need for a second light source is shown in FIG. 12. Light from light source 10 is emitted along optical axis BB through input lens 6 and output lens 7 through input aperture 15 of integrating hemisphere 13 to impinge on the inside surface 12 of integrating sphere 11. Light is diffusely reflected by multiple incidences between inside surface 12 of the integrating sphere to emerge along optical axis 55 at exit aperture 16 of integrating sphere 11. Optical surface 62, by example selectable by rotation about axis of rotation 63 with at least one transmitting surface or aperture 64 and at least one reflecting area 62 is positioned beyond the exit aperture 16 of integrating hemisphere 13 to reflect light substantially 90 degrees to optical axis 55 along optical axis 68 or transmit light along optical axis 55 dependent upon the alignment of aperture 64 or reflecting area 62 to optical axis 55. Positioning of reflecting surface 62 along optical axis 55, reflects light emerging from exit aperture 16 to impinge upon transmit detector 17 positioned along optical axis 68, thus a measure of the transmitted light from light source 10 is ascertained. Positioning aperture 64 along optical axis 55 permits the transmission of light along optical axis BB through central aperture 58 of meniscus lens 1 by relay of emitted light from exit aperture 16 through aperture stop 65, lens 66, optical fiber 67, and lens 57. An image of the end of optical fiber 67 is formed at the concave surface of meniscus lens 1 through central aperture 58 synonymous to the image 9' of field stop 9, to impinge upon particle detector 5 in proportion to the light detected by transmit detector 17 by means of field lens 2, and lens 3, field stop 9, and lens 4.

I claim:

1. A measurement system comprising:
    a light source directed along a first axis and configured to illuminate a sample volume;
    a first sensor aligned along a second axis and configured to detect scattered light in the sample volume;
    a first lens system aligned along the second axis and located between the sample volume and the first sensor, first sensor, with the first lens system comprising:
    a first reflecting lens aligned along the second axis where the first reflecting lens has a first focus on the second axis and a second focus on the second axis where the second focus is between the first focus and the first reflecting lens and where the second focus is positioned in the sample volume;
    a first field lens located on the second axis and positioned such that the second focus of the first reflecting lens occurs inside the first field lens;
    a first relay lens system aligned to the second axis where the first relay lens system forms a first focus at the second focus of the first reflecting lens;
    a second sensor aligned along a third axis and configured to detect scattered light in the sample volume; and
    a second lens system aligned along the third axis and located between the sample volume and the sensor, with the second lens system comprising:
    a second reflecting lens aligned along the third axis where the second reflecting lens has a first focus on the third axis and a second focus on the third axis where the second focus is between the first focus and the second reflecting lens and where the second focus is positioned in the sample volume;
    a second field lens located on the third axis and positioned such that the second focus of the second reflecting lens occurs inside the second field lens;
    a second relay lens system aligned to the third axis where the second relay lens system forms a first focus at the second focus of the second reflecting lens.

2. The measurement system of claim 1 where the first, second and third axis are all orthogonal.

3. The measurement system of claim 1 where die first sensor is configured to detect light over a different wavelength band than the second sensor.

4. The measurement system of claim 1 where the first sensor is configured to detect light over a different intensity range than the second sensor.

5. The measurement system of claim 1 further comprising:
    a first mask located on the second axis and configured to limit the light that reaches the first sensor;
    a second mask located on the third axis and configured to limit the light that reaches the second sensor.

6. The measurement system of claim 5 where the first mask is configured to limit the light that reaches the first sensor to a first predetermined angle of scatter and the second mask is configured to limit the light that reaches the second sensor to a second predetermined angle of scatter where the first predetermined angle of scatter is different than the second predetermined angle of scatter.

7. The measurement system of claim 1 further comprising:
    an integration sphere including an entrance port and an exit port where the integration sphere is on the first axis opposite the light source and the entrance port is aligned with the first axis;
    a detector aligned with the exit port and configured to detect the intensity of light in the integration sphere.

8. A method of operating a measurement system, comprising:
    illuminating a volume with a light source along a first axis;
    aligning a first lens system along a second axis with a first focus located inside the volume and where the second axis is different than the first axis;
    locating a first sensor at a second focus of the first lens system on the second axis and where the first sensor is configured to detect scattered light near the first focus, with the first lens system comprising:
    a first reflecting lens aligned along the second axis where the first reflecting lens has a first focus on the second axis and a second focus on the second axis where the second focus is between the first focus and the first reflecting lens and where the second focus is positioned in the sample volume;
    a first field lens located on the second axis and positioned such that the second focus of the first reflecting lens occurs inside the first field lens;

a first relay lens system aligned to the second axis where the first relay lens system forms a first focus at the second focus of the first reflecting lens;

aligning a second lens system along a third axis with a third focus located inside the volume and where the third axis is different than the first and second axis;

locating a second sensor at a fourth focus of the second lens system on the third axis and where the second sensor is configured to detect scattered light near the third focus, with the second lens system comprising:

a second reflecting lens aligned along the third axis where the second reflecting lens has a first focus on the third axis and a second focus on the third axis where the second focus is between the first focus and the second reflecting lens and where the second focus is positioned in the sample volume;

a second field lens located on the third axis and positioned such that the second focus of the second reflecting lens occurs inside the second field lens;

a second relay lens system aligned to the third axis where the second relay lens system forms a first focus at the second focus of the second reflecting lens.

9. The method of operating a measurement system of claim 8, further comprising:

locating a first mask on the second axis where the first mask is configured to limit the light that reaches the first sensor;

locating a second mask on the third axis where the second mask is configured to limit the light that reaches the second sensor.

10. The method of operating a measurement system of claim 9 where the first mask is configured such that the first sensor detects light selected from the following: back scattered light, front scattered light, or side scattered light.

11. The method of operating a measurement system of claim 8 where the first sensor is configured to detect light over a different wavelength band than the second sensor.

12. The method of operating a measurement system of claim 8, further comprising:

integrating;

locating a second mask on the third axis where the second mask is configured to limit the light that reaches the second sensor.

13. A measurement system comprising:

a plurality of light sources directed along a plurality of axes where each of the plurality of light sources is configured to illuminate a single sample volume;

a plurality of corresponding light detectors aligned with the plurality of axes and configured to detect unscattered light passing substantially through the single sample volume; and a first sensor aligned along a second axis that is distinct from the plurality of axes, and configured to detect scattered light in the single sample volume; and a lens system aligned along the second axis and located between the single sample volume and the first sensor, with the first lens system comprising:

a first reflecting lens aligned along the second axis where the first reflecting lens has a first focus on the second axis and a second focus on the second axis where the second focus is between the first focus and the first reflecting lens and where the second focus is positioned in the sample volume;

a first field lens located on the second axis and positioned such that the second focus of the first reflecting lens occurs inside the first field lens;

a first relay lens system aligned to the second axis where the first relay lens system forms a first focus at the second focus of the first reflecting lens.

14. A measurement system comprising:

a means for illuminating a sample volume along a first axis;

a means for detecting transmitted light passing substantially through the sample volume;

a first means for detecting scattered light in the volume of illumined light along a second axis;

a first means for focusing the scattered light along the second axis and forming an image for the first means for detecting the scattered light, with the first means for focusing the scattered light including a first reflecting lens aligned along the second axis where the first reflecting lens has a first focus on the second axis and a second focus on the second axis where the second focus is between the first focus and the first reflecting lens and where the second focus is positioned in the sample volume;

a second means for detecting scattered light in the volume of illumined light along a third axis; and a second means for focusing the scattered light along the third axis and forming an image for the second means for detecting the scattered light.

* * * * *